United States Patent [19]
Alderson

[11] Patent Number: 5,769,779
[45] Date of Patent: Jun. 23, 1998

[54] METHOD AND APPARATUS FOR ACCURATE RADIATION DOSAGE CONTROL IN BREAST CANCER TREATMENT

[75] Inventor: Samuel W. Alderson, Beverly Hills, Calif.

[73] Assignee: Radiology Support Devices, Inc., Long Beach, Calif.

[21] Appl. No.: 429,477

[22] Filed: Apr. 27, 1995

[51] Int. Cl.⁶ .................................................. A61N 5/00
[52] U.S. Cl. .................................................. 600/1; 600/3
[58] Field of Search ............................................. 600/1–8

[56] References Cited

U.S. PATENT DOCUMENTS

| | | | |
|---|---|---|---|
| 3,310,885 | 3/1967 | Alderson | 35/17 |
| 3,365,575 | 1/1968 | Strax | 250/50 |
| 5,083,305 | 1/1992 | Tirelli et al. | 378/37 |
| 5,095,499 | 3/1992 | Wentz | 378/37 |
| 5,115,134 | 5/1992 | Slowey | 250/374 |

OTHER PUBLICATIONS

Bentel et al., "A Simple Device to Position Large/Flaccid Breasts During Tangential Breast Irradiation," *Int. J. Radiation Oncology Biol. Phys.* 29(4) 879–882 (1994).
Ciocca et al., "Quality Control in the Conservative Treatment of Breast Cancer: Patient Dosimetry Using Silicon Detectors," *Radiotherapy and Oncology* 22 304–307 (1991).
Conway et al., "A Patient–Equivalent Attenuation Phantom for Estimating Patient Exposures from Automatic Exposure Controlled X–ray Examinations of the Abdomen and Lumbo–Sacral Spine[a]," *Med. Phys.* 17(3) 448–453 (1990).

Hamers et al., "In Vivo Dosimetry with TLD in Conservative Treatment of Breast Cancer Patients Treated with the EORTC Protocol 22881," *Acta Oncologica* 32(4) 435–443 (1993).
Knöös et al., "Comparison of Measured and Calculated Absorbed Doses from Tangential Irradiation of the Breast," *Radiology and Oncology* 7 81–88 (1986).
McParland et al., "The Effect of a Dynamic Wedge in the Medial Tangential Field Upon the Contralateral Breast Dose," *Int. J. Radiation Oncology Biol. Phys.* 19 1515–1520 (1990).
van Bree et al., "Three–Dimensional Dose Distribution of Tangential Breast Treatment: A National Dosimetry Intercomparison," *Radiotherapy and Oncology* 22 252–260 (1991).

*Primary Examiner*—John P. Lacyk
*Attorney, Agent, or Firm*—Christie, Parker & Hale, LLP

[57] ABSTRACT

The present invention pertains to a method and apparatus for accurately monitoring radiation dosage to a patient. The invention provides a treatment brassiere having a visually transparent cup that consistently shapes and places a patient's breast for delivery of radiation therapy. The brassiere can also have shaping portion for shaping the contralateral breast such that it is positioned as far away from radiation treatment as possible. The shaping portion can additionally have dosimeters attached for measuring the radiation delivered to the skin of the contralateral breast and can have radiation absorbent material attached to the shaping portion to further protect the contralateral breast from radiation. The invention provides an overall method of consistent radiation therapy for a tumorous breast.

19 Claims, 8 Drawing Sheets

METHOD AND APPARATUS FOR ACCURATE RADIATION DOSAGE CONTROL IN BREAST CANCER TREATMENT

FIELD OF THE INVENTION

The present invention relates to a method and apparatus for achieving accurate treatment and monitoring of radiation dosage to a tumorous breast being treated as well as accurate monitoring of the skin of the contralateral breast and surrounding body tissue in the treatment of breast cancer by radiation.

BACKGROUND OF THE INVENTION

In the United States, it has been estimated that 182,000 new cases of breast cancer in women would result in 1994 with 46,000 fatalities. American Cancer Society in *Cancer Facts and Figures*-1994. One of the most generally accepted protocols for breast cancer treatment is a lumpectomy, followed by uniform dosage of radiation treatment throughout the breast. In designing and carrying out such a treatment plan, it is desirable to determine the effect of the radiation dosage to the breast being treated as well as the surrounding areas of the body. It is also desirable to determine as accurately as possible, the dosage which will be received by the breast being treated and to monitor the effects of such dosage on other areas of the body, including common lines of spread; dosage to the skin of the contralateral breast; and dosage to the adjacent body tissue. Better quality control of dosage and monitoring of dosage would be expected to significantly reduce the number of deaths and improve response to radiation treatment.

There are many treatment programs which try to provide adequate quality assurance measures. One such procedure is to measure entrance and exit doses of radiation and interpolation of the data to determine dosage to intervening tissues. However, measurement of entrance and exit doses with interpolation is limited to use of a few actual measurement points. Actual dosage to the areas where interpolation has been performed does not always accurately follow from the entrance and exit doses.

Another treatment procedure is surgical implantation of tubes, generally under full anesthesia, into which thermoluminescent dosimeter (TLD) rods may be inserted through the midplane of the tumor and in single planes above and below the midplane. Unfortunately, surgical implantation of tubes is an invasive procedure requiring full anesthesia. There are also a relatively limited number of dosage test points.

Another monitoring procedure is to rely on a single skin dose measurement as a checkpoint for the treatment plan. This procedure, however, gives the treating physician very little useful information on the actual dosage delivered deep into the affected tissue and surrounding body.

Another testing method for a treatment plan is to test a radiation phantom. An example of a radiation phantom is disclosed in U.S. Pat. No. 3,310,885 to Alderson, the present inventor. One such phantom is called the RANDO phantom, which has been made with breast adaptors into which TLDs can be inserted and a prescribed radiation treatment can thus be carried out on the phantom with the adaptor. Although such a system has the advantage of being able to use many TLD devices to achieve many measurements, the positioning of the phantom torso and adaptor, and the size and shape of the adaptor is not necessarily repeatable and does not necessarily correspond to the actual positioning, size and shape of the patient's breast and surrounding tissue. A plastic cup strapped to the patient's breast has thus been used to shape the breast of the patient to conform somewhat with the phantom breast adaptor.

Existing monitoring schemes and methods do not achieve a sufficient set of dosimetric points to guard against hot or cold test spots; to take into account field distortions, such as when the radiation beam or beams pass through the tips of the lung; to measure and control the potentially carcinogenic dose to the contralateral breast; and to assure adequate dosage to the most common lines of spread, such as spreading to the axillary lymph nodes. In addition, it would be desirable for a system to provide a relatively comprehensive mapping of dosages and yet a process simple enough and quick enough to follow by a radiation technologist in a busy radiation therapy department. In addition, it would be desirable for the patient and phantom to be as closely matched as practicable in position on the treatment table, size and shape of the breast and adjacent tissues, positioning of the breast relative to landmarks of the patient's anatomy and in soft tissue equivalence between the patient and phantom.

SUMMARY OF THE INVENTION

The present invention overcomes the above problems and pertains to a method and apparatus for accurately monitoring radiation dosage to a patient. In one embodiment, the invention provides a treatment brassiere for radiation therapy of a breast of a patient. The brassiere has a visually transparent cup having a predetermined shape which holds a patient's breast in the predetermined shape and at a desired position with respect to the patient's body by means of a strap or other device to fix the cup to the patient's body. The brassiere preferably includes a mechanism to hold the contralateral breast remote from the breast being treated with radiation. The cup is preferably attached to the brassiere by a releasable attachment system so that other cups could be used with the brassiere.

In a more preferred embodiment, the mechanism to hold the contralateral breast remote from the breast being treated comprises a Posicast® material which is capable of holding TLDs to measure and thereby monitor radiation dosage to the skin of the contralateral breast during actual treatment. It is further preferred to provide a radiation absorbent material such as lead foil wrapped around the mechanism to hold the contralateral breast. The cup preferably has holes formed therein for consistent placement of the cup and for increasing a skin sparing effect of the radiation treatment. In another embodiment, the invention includes a set of brassiere cups of varying shapes and sizes.

In an additional embodiment, the invention includes a set of breast adaptors for a radiation therapy phantom for testing radiation dosage effects, the breast adaptors having varying sizes and shapes and being capable of releasable attachment to a radiation therapy phantom torso in a position and shape that closely correspond to the patient's anatomy. In addition, thermoluminescent dosimeter (TLD) holders in the breast adaptor are preferably made in a pattern consistent with the pattern of holes in the phantom torso.

In a further embodiment, the invention provides a three dimensional measuring device for consistent positioning of a patient or phantom or both, with respect to a treatment table and consistent positioning of the breast to be treated or breast adaptor of the phantom. The device includes a base, a post connected to the base, a mechanism to mount the device to a fixed position with respect to a treatment table, a cranial-caudal bar connected to the post for measuring the cranial-caudal location of the patient or phantom relative to the three dimensional measuring device, a lateral bar connected to the cranial-caudal bar for measuring the lateral location of the patient or phantom relative to the three dimensional measuring device, and an anterior-posterior bar connected to the lateral bar for measuring the anterior-posterior location of the patient or phantom relative to the measuring device.

In yet another embodiment, the invention provides a method for consistently placing a patient's breast in the same position and shape for receiving radiation treatments, including placing the patient in a supine position on a radiation treatment table, placing the patient's breast to be treated in a visually transparent cup having a predetermined shape, and fixing the cup to the patient's body with the cup over the patient's breast to be treated. In a preferred embodiment, the cup is constructed as in the brassiere discussed above. In another preferred embodiment, the cup has a plurality of holes for marking the patient's breast with a permanent marker to form at least three or more marks on the breast or surrounding portions of the patient to consistently place the cup. Preferably, one of the holes of the cup is at the apex of the cup, one hole is at the medial edge of the cup, and one hole is at the lateral edge of the cup. The patient's breast is then permanently marked at these three positions. It is preferred in this method to determine the position of the mark or marks using a three dimensional measuring device such as the above device, for measuring these locations relative to a fixed point, such as the sternal notch of the patient's body.

In a still further embodiment, the invention provides an overall method of radiation therapy for a tumorous breast including the steps of placing a visually transparent cup over a patient's tumorous breast and aligning the tumorous breast with respect to a fixed reference using the visually transparent cup and a measuring device to determine the patient's location and the breast's location in three dimensional space with respect to the fixed reference, removing the patient from the fixed reference and placing a phantom including a phantom breast adaptor capable of monitoring radiation dosage on the fixed reference and aligning it with respect to the fixed reference in the same location as the patient and the patient's breast was, applying radiation to the phantom breast in accordance with a selected radiation treatment plan for the tumorous breast, analyzing the radiation dosage results of the radiation treatment to the phantom breast and, if necessary, revising the treatment plan and repeating the above steps of placing the phantom on the fixed reference and applying the radiation to it until the radiation results are as desired, removing the phantom and placing the patient with the cup over the patient's tumorous breast at the same location with respect to the fixed reference, and treating the patient's tumorous breast with selected radiation treatment. The method further includes a preferred step of monitoring radiation dosage to the skin of the contralateral breast during treatment of the patient.

As will be realized, the invention is capable of other and different embodiments and its several details are capable of modification in various respects, all without departing from the spirit and scope of the present invention. Accordingly, the drawings and detailed description are to be regarded as illustrative in nature and not as restrictive.

BRIEF DESCRIPTION OF THE DRAWINGS

The above and other aspects and advantages of the invention will become more evident upon reading the following detailed description in conjunction with the drawings in which.

DETAILED DESCRIPTION OF THE PREFERRED EMBODIMENTS

In one embodiment, the present invention provides a breast radiation therapy treatment system including several new and non-obvious aspects including an overall system which is new and non-obvious. An important purpose of the treatment system is to consistently position the breast being treated and consistently shape it for radiation treatment, so that such radiation treatment is consistent with radiation dosage testing performed on a radiation therapy phantom such as shown in U.S. Pat. No. 3,310,885 to Alderson incorporated by reference herein, and as made under the name ART phantom BY Radiological Support Devices, Inc. (RSD) of Long Beach, Calif. Thus, as part of the system, the radiation therapy phantom and a breast adaptor for it must be made consistent with the patient's location and anatomy. In addition, it is preferred to monitor the actual dosage to the contralateral breast during treatment.

Figure 1:
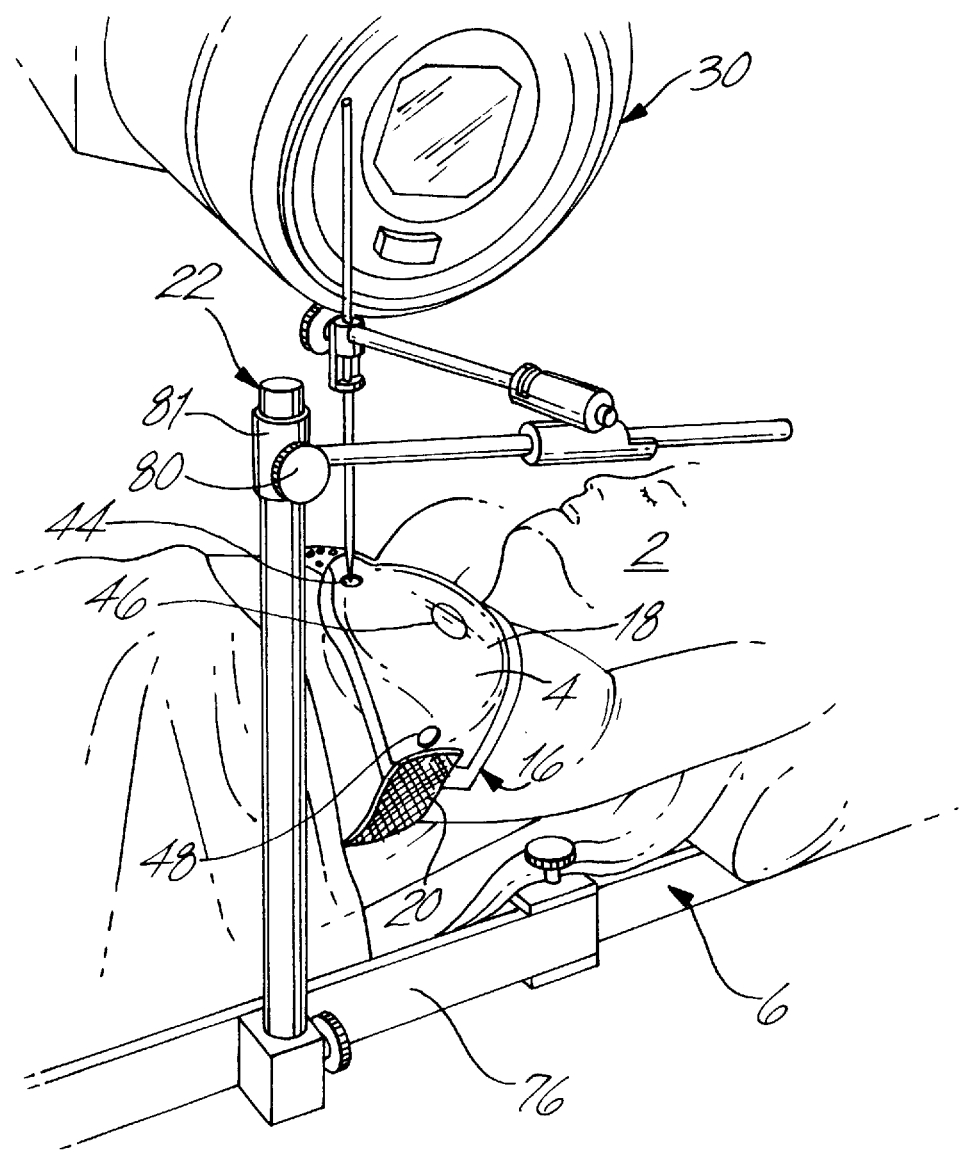
FIG. 1 is a perspective view of a patient on a radiation treatment table having a three dimensional measuring device according to the invention affixed thereto, and the patient having a brassiere in accordance with the invention, the patient being shown adjacent a radiation treatment device.
Figure 4:
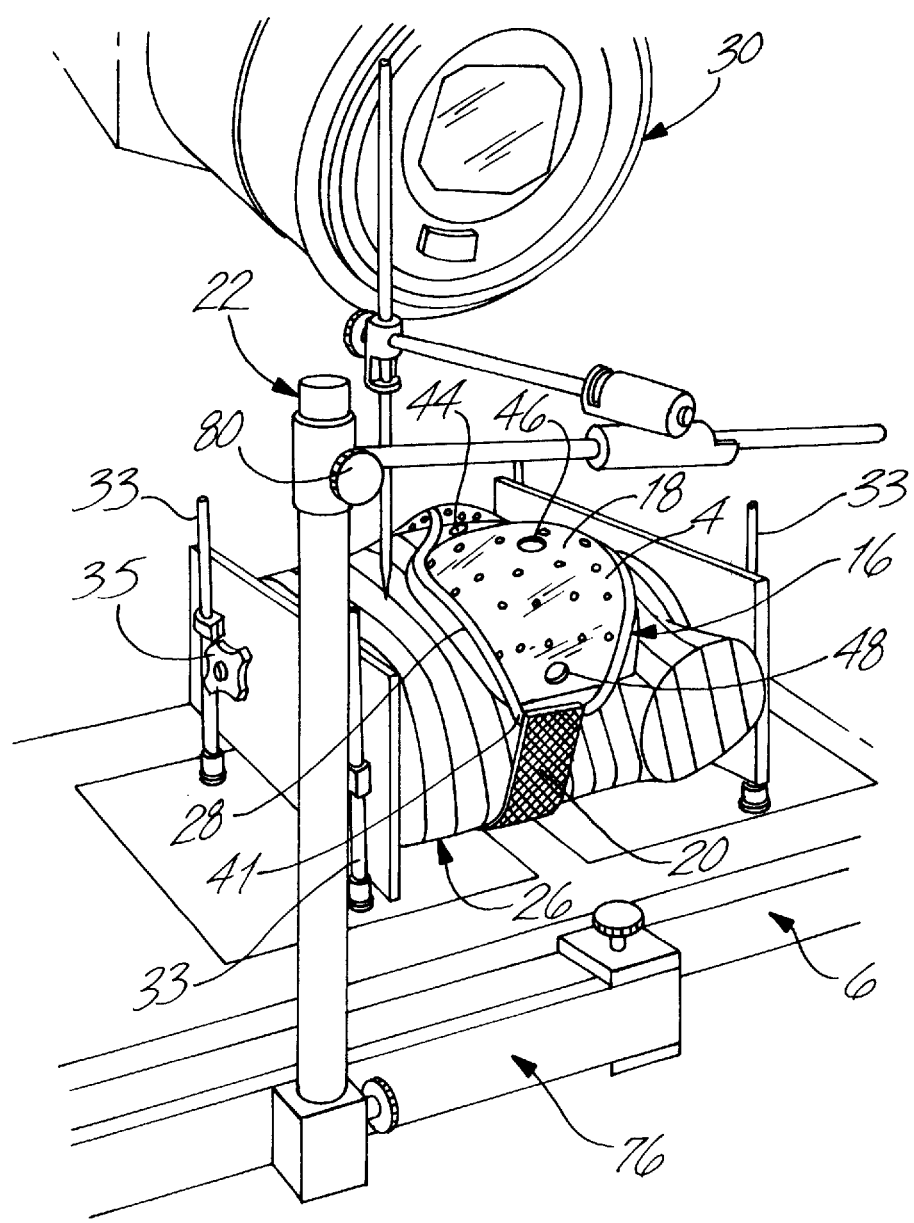
FIG. 4 is a perspective view similar to that of FIG. 1, except that a phantom with a breast adaptor and brassiere in accordance with the invention is shown on the treatment table instead of a patient.

With reference to FIGS. 1 and 4, the system includes a brassiere 16 with a clear plastic cup 18 for holding the breast 4 of a patient 2 in a repeatable shape and position. The brassiere has a main strap 20 for wrapping around the patient or a radiation therapy phantom torso 26. The system also includes a measuring device 22, preferably fixed to a treatment table 6, to accurately measure in three dimensions the location of the patient and the patient's breast with respect to the table 6. The system further includes a radiation therapy phantom torso 26 with a breast adaptor 28 which preferably matches the shape and size of cup 18 which best fits the breast 4 of the patient 2. The phantom with the breast adaptor is used to measure radiation dosage at several points on the breast adaptor and surrounding areas in order to determine an appropriate radiation treatment plan for actual use on the patient.

Figure 5:
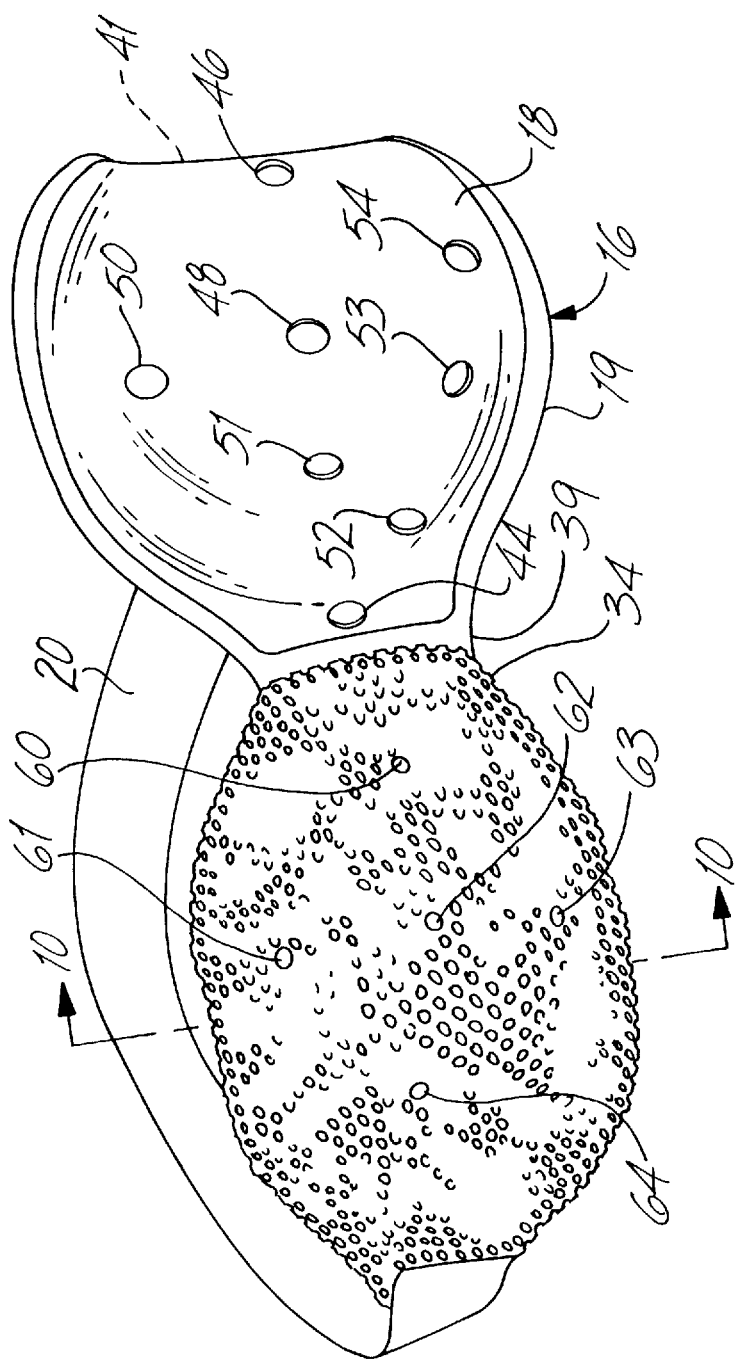
FIG. 5 is a perspective view of a brassiere such as that of FIG. 1 having holes formed in a visually transparent cup for the breast being treated and having a Posicast® material forming a cup for the contralateral breast.
Figure 6:
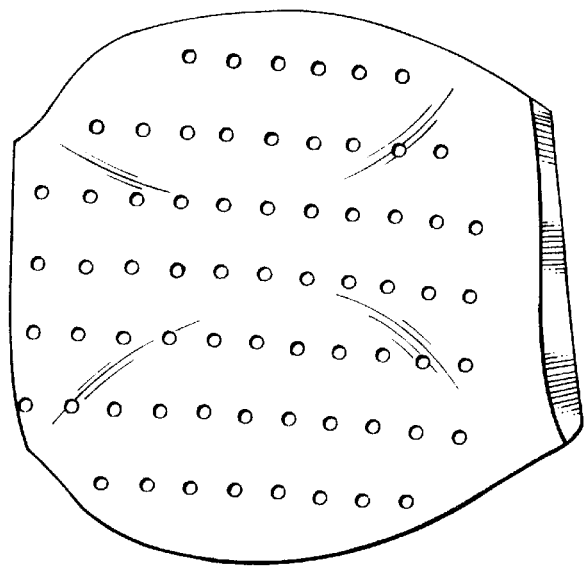
FIG. 6 is a front view of the breast adaptor such as that shown in FIG. 4.
Figure 7:
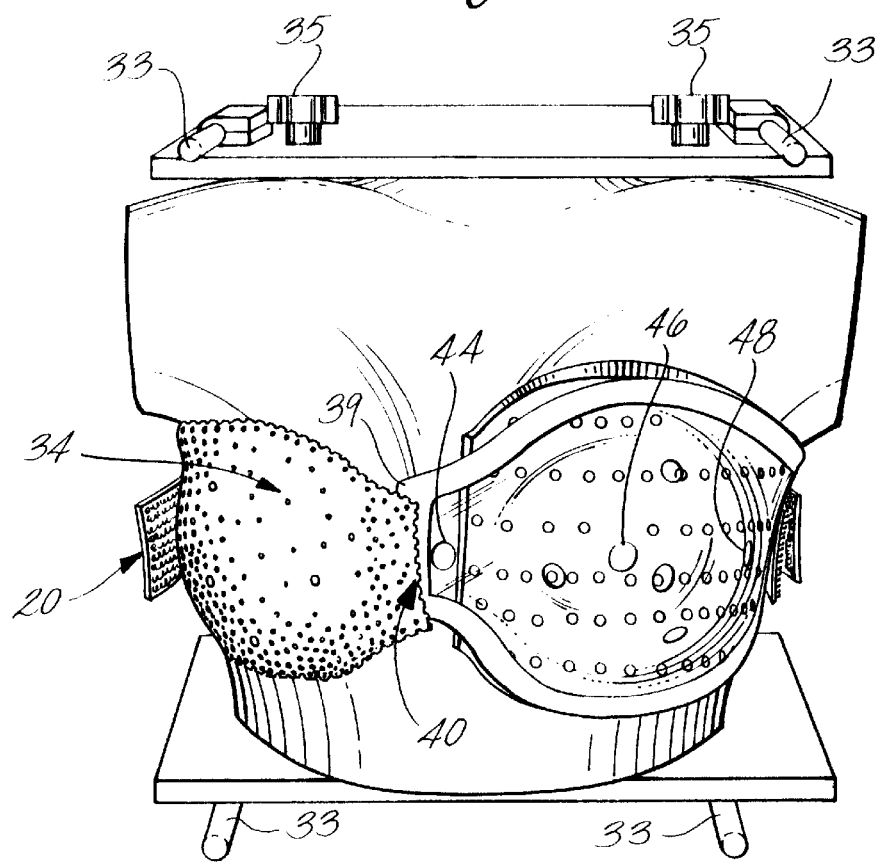
FIG. 7 is a plane view of the phantom torso and breast adaptor and brassiere such as shown in FIG. 4.

Current radiation dosimetry plans are based upon a number of factors including the location or former location of the tumor(s), any areas of possible or likely spread of the tumor(s), minimization of radiation dosage to non-affected areas, and numerous other factors. To perform the testing on the phantom, and to make sure the phantom position on the treatment table in relation to the table and radiation source 30 is consistent with that of the patient, the dimensions recorded from the patient laying on the treatment table as in FIG. 1 are used to set up the phantom and breast adaptor, as shown in FIG. 4. A radiation treatment program is then delivered to the phantom. Measurements of the actual radiation delivered to the phantom are then made and compared to an ideal radiation treatment program for the individual patient. Adjustments to the treatment program are then made until the actual program and the ideal program correspond. Once a suitable treatment program is selected, the patient 2 is again positioned on the treatment table 6 as shown in FIG. 1 in the same consistent position using the measuring device 22 and brassiere 16. The radiation treatment program is then applied to the patient. The brassiere, which is best shown in FIG. 5, also has a protective portion 34 which has been shaped to the contralateral breast in such a way as to hold the contralateral breast as remote as possible from the breast 4 being treated. In addition, the protective portion 34 is constructed to hold TLDs and thus monitor actual dosage to the skin of the contralateral breast during radiation treatments to the patient. The protective portion 34 could also have a material attached to it to shield the collateral breast from radiation.

Figure 8:
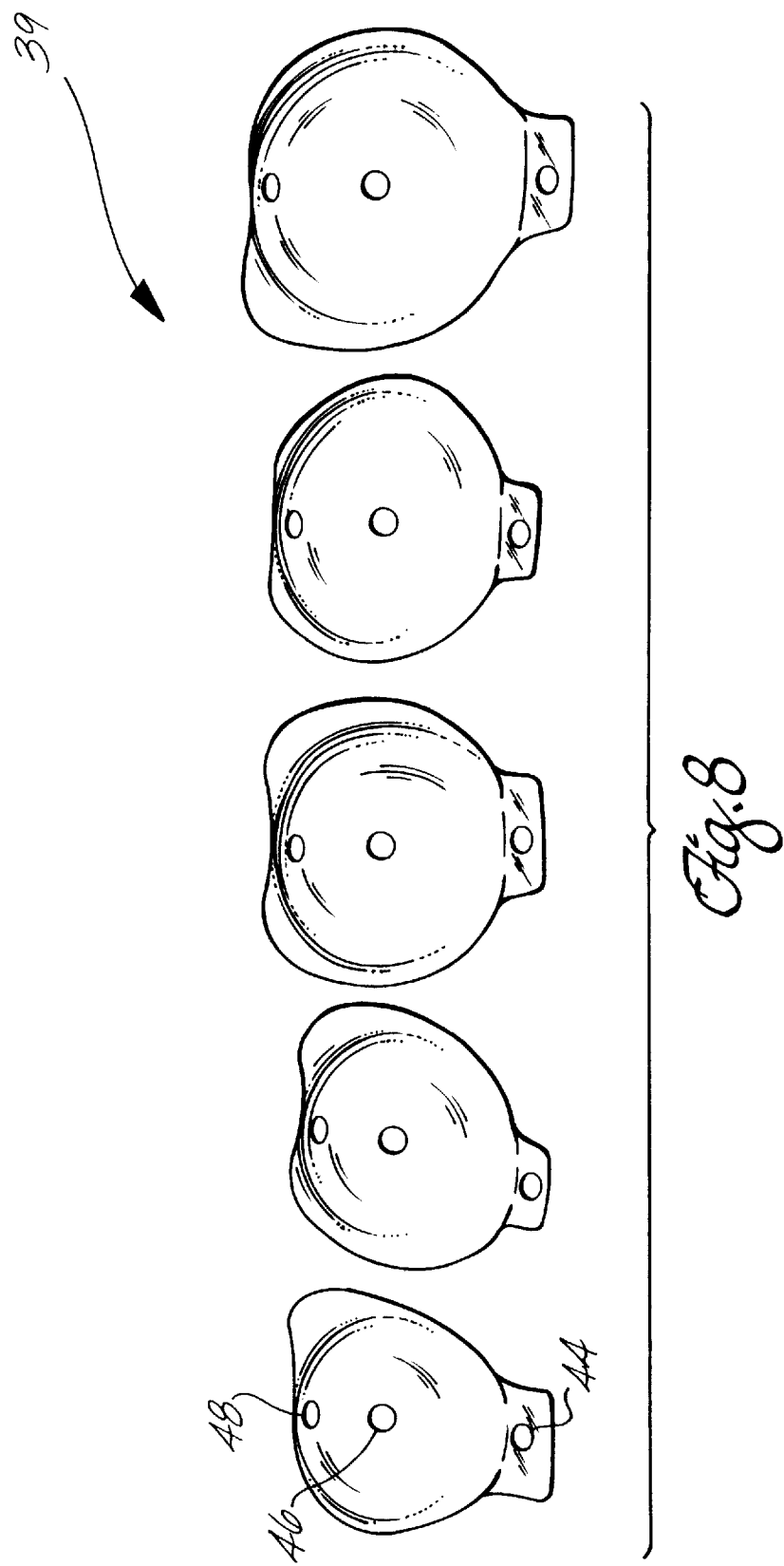
FIG. 8 is a view of a library of visually transparent cups for the brassiere of FIG. 5.

Generally, the first step of the radiation treatment therapy is to select a cup from a set of cups. The set would preferably include each of six standing brassiere cup sizes A–DDD for the left and right breasts, and different shapes for each size breast, e.g., six different breast shapes for each cup size for each side. This would provide a total of 72 cups in the typical library. Examples of representative different cup shapes are illustrated in FIG. 8. The cups are preferably a clear thermoplastic material. The cup which best fits the patient may be used as the actual cup to form the patient's brassiere 16, or, preferably, a duplicate of that cup is made to order or in stock. Cups are made of a polyester material such as PETG co-polyester, e.g., made by Lustro Plastics Co. of Las Vegas, Nev. Cups can be custom formed if need be using a thermoplastic material such as POSICAST® which becomes malleable after immersion in a hot water bath. The cup would then be dried such as by use of a towel and once at a comfortable temperature level, placed onto the patient's breast, which preferably would be fitted with a plain cotton brassiere. The material would then be shaped to the breast by a technician and would harden in that shape as the material cools. The material would then be used as a mold for vacuum forming an actual custom breast cup of a clear plastic, relatively rigid or semirigid material that will hold the breast in the desired shape. A cup library as discussed above may be formed using the same method as the custom forming method just described, by repeating the process using subjects for each breast size and each desired shape in each size. The 72 cup library discussed above should suffice for most patients without the need to custom form a cup, as such a library is expected to meet the needs of about 95% of the patients. The remaining 5% of patients would need a custom made cup.

With renewed reference to FIG. 5, the selected cup is then fitted into a sheath 19 attached around the periphery of the cup, which sheath may be stitched or otherwise fastened to the cup. It is expected that the treatment facility will determine the appropriate cup and a supplier, such as Radiological Support Devices (RSD) in Long Beach, Calif., would prepare the brassiere using an identical cup as the one selected from the library, e.g., by identifying each cup by a number such as 1 through 72.

As shown in FIG. 5, each cup has a medial flange 39 at which portion the contralateral breast protective shaper 34 is fixed, e.g., by means of adhering a hook or loop strip such as a hook or loop Velcro® strip to the medial underside of shaper 34. Each cup also has lateral flange 41 with a Velcro® type strip to the medial underside of shaper 34. Each cup also has a lateral flange 41 with a Velcro® strip so that one end of the main strap 20 with Velcro® may adjustably mate with it. The other end of strap 20 also has Velcros strip for mating with a Velcro® strip adhered to the lateral end of the shaper 34. Other suitable means of attachment will be evidence to those of ordinary skill in the art. The Velcro® strips are not shown, as Velcro® is well known in the art.

The plastic cup preferably has a hole or holes formed therein. As shown in FIG. 5, there are patient alignment holes 44, 46, and 48, preferably adjacent the patient's medial line, lateral side, and cup apex, respectively. These holes may be preformed in the cup or formed after the appropriate cup is selected, and the patient's skin is permanently marked through these holes in order to assist with alignment as described later. Holes 50–54 are used to achieve an unimpeded skin sparing effect and assist the radiologist in assessing the skin sparing effect on the areas where there are no holes. The placement, size, and number of holes vary as desired, e.g., five holes of 1.5 centimeters diameter each. It is also noted that the number and placement of alignment holes may vary as desired, although three as shown is preferred. Holes 44, 46, and 48 may be on the order of 1.5 centimeters in diameter, although the size of the alignment holes may also vary. In addition, to minimize loss of the skin sparing effect, the thermoplastic material of the cup should be thin, e.g., 4 mm to 8 mm.

Figure 10:
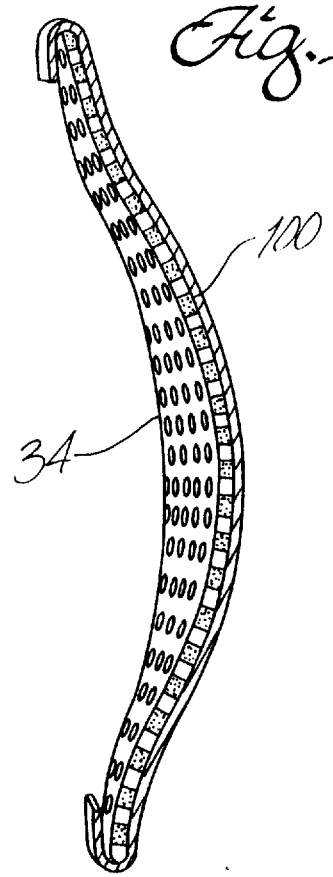
FIG. 10 a sectional view taken along the line 10—10 of the brassiere of FIG. 5 and further including an overlapping lead foil layer.

The contralateral breast protective shaper 34 preferably is formed by a material such as Posicast® which can be immersed in hot water, towel dried and then be malleable to conform to and help position the contralateral breast remote from the breast to be treated. The material will then harden as it cools to room temperature. The Posicast® material preferably has numerous holes formed therein, as shown in FIG. 5, some of which holes may have TLD holders 60–64 disposed therein which hold TLDs for measuring dosage to the contralateral breast during actual treatment and/or during radiation testing on the phantom. As illustrated in FIG. 10, the protective portion can be covered with a solid lead foil 100 and wrapped around the edges of the protective portion to hold the lead foil in place. The lead foil absorbs radiation and adds additional protection to the contralateral breast to help shield the contralateral breast from radiation.

Once the patient 2 is fitted with an appropriate cup 18 and protective shaper 34, the cup and protective shaper are strapped around the patient using strap 20 (see FIG. 1). The patient is then placed supine on a treatment table 6. The three dimensional alignment of the patient with respect to the table and the radiation source 30 is then measured by using the three dimensional measuring device 22 as described below. A radiation treatment plan can then be delivered directly to the patient. When the patient returns over time to receive additional radiation treatments, the brassiere with the cup and shaper is again placed on the patient. The cup is placed on the patient in the same location as originally placed on the patient by aligning the marks placed on the skin of the patient with the alignment holes 44, 46, and 48.

The patient is then placed supine on the treatment table and positioned identically as the original positioning using the three dimensional measuring device 22 and the measurements previously made. A consistent radiation treatment plan over time can then be delivered to the patient.

A more preferred treatment program is to use a radiation phantom torso 26 with a breast adaptor 28 to test the radiation treatment program. With reference to FIG. 4, before the patient receives a radiation treatment program, a radiation treatment program is delivered to a radiation phantom. This is done after the patient has been fitted with the cup 18 and shaper 34 and the patient's three dimensional location on the treatment table 6 has been measured. The patient is removed from the treatment table and a radiation phantom torso is then placed on the table. The phantom is fitted with a breast adaptor 28 as described below. The cup 18 and shaper 34 are then strapped to the phantom and the breast adaptor using strap 20. The phantom is then aligned in the exact same three dimensional alignment as the patient was aligned using the three dimensional measurements made and the three dimensional measuring device 22. An experimental radiation treatment plan is then delivered to the phantom and breast adaptor using radiation source 30. The phantom and adaptor have TLDs placed throughout as described below. The TLDs measure the radiation actually delivered to the TLDs. The treating professional can then analyze the actual radiation delivered to the phantom and breast adaptor and correlate the radiation delivered to an ideal treatment plan for the particular patient. If the actual plan and the ideal plan vary, adjustments can be made to the radiation treatment plan until the actual plan and the ideal plan correspond. Once the proper treatment plan has been selected and confirmed by use of the phantom and breast adaptor, the patient is then again placed on the treatment table. The alignment of the cup is confirmed using the marks made on the patient and the alignment holes. The three dimensional alignment of the patient is confirmed using the three dimensional measuring device and the measurements previously taken. The patient is then given the radiation treatment plan. The above steps are repeated as needed over time to ensure that the patient is receiving a consistent radiation treatment program customized for that particular patient.

Figure 2:
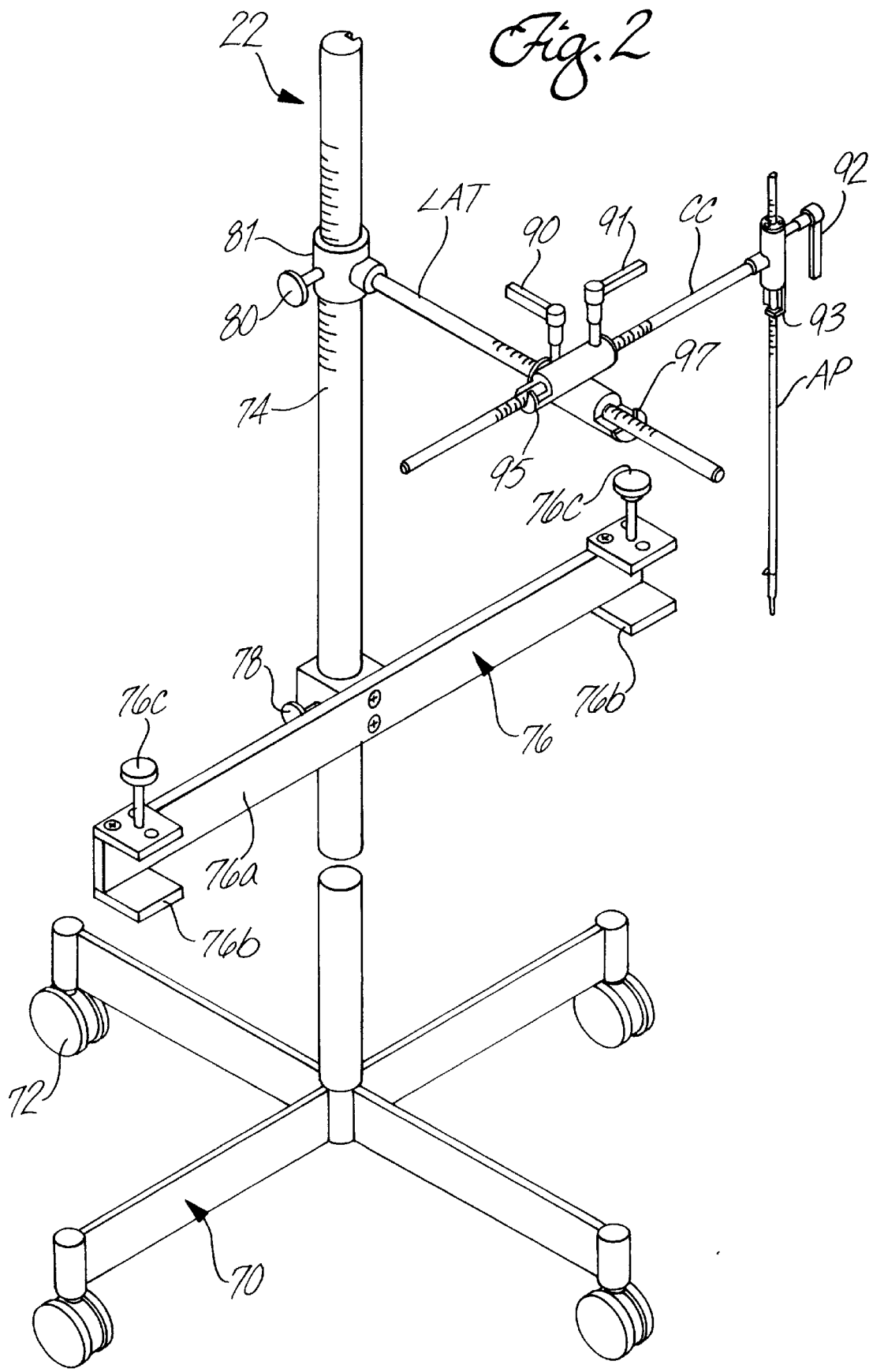
FIG. 2 is a perspective view of the measuring device of FIG. 1.
Figure 9:
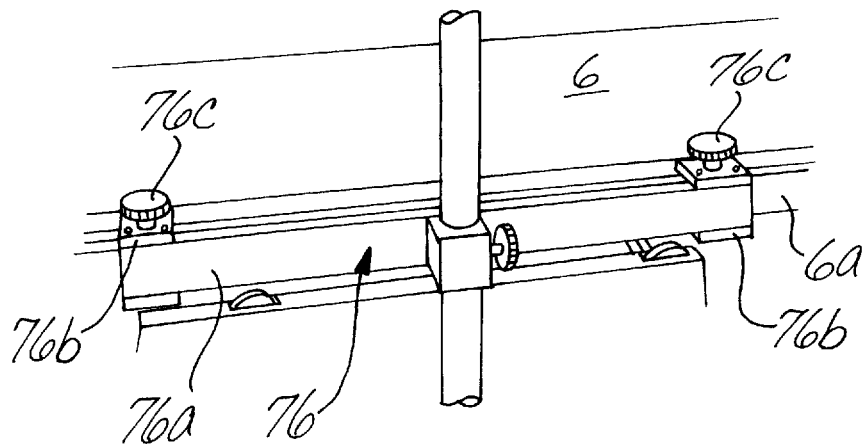
FIG. 9 is an enlarged view of a portion of the three dimensional measuring device of FIG. 2 showing its attachment to the treatment table.

The three dimensional measuring device 22 is shown in detail in FIG. 2. The three dimensional measuring device forms an orthogonal system with three degrees of freedom. The device has a base 70 with wheels 72, a vertical post 74 mounted on top of base 70, a clamping device 76 vertically movable along post 74 and fixable to post 74 by a threaded knob 78 (a standard threaded rod with a plastic handle), and three measuring bars LAT, CC, and AP which are mutually orthogonal and are vertically movably attached on post 74 using a threaded knob 80. The clamping assembly 76, as shown in FIG. 9, has a horizontal bar 76a, and two C-shaped clamping elements 76b for fitting to the side 6a of treatment table 6 and being fixed thereto by threaded knobs 76c. The post 74 and three measuring bars all preferably have gradations which are numbered or otherwise distinguishable. With the device clamped to the side of the treatment table, such as shown in FIG. 1, knob 80 is loosened to move a slidable cylindrical ring 81 to a height above the patient (or phantom) at which the three measuring bars can be readily used. Measurements should be taken preferably as shown in Table I below.

TABLE I

Patient Code (for use by treatment centers only) _____
Cup Number _____
ALIGNMENT DIMENSIONS RELATIVE TO TABLE Sternal notch to table top (AP) _____
Laser landmark to table top (AP) _____
Sternal notch to landmark (CC dimension) _____
DIMENSIONS RELATIVE TO SKELETON LANDMARK CC Dimensions CC bar reader to sternal notch _____
CC bar reader to breast cup apex _____
Sternal notch to breast cup apex _____
AP Dimensions AP bar reader to Breast cup apex _____
AP bar reader to Sternal notch _____
Sternal notch to breast cup apex _____
Lateral Dimensions LAT bar reader to Breast cup apex _____
LAT bar reader to Sternal notch _____
Sternal notch to breast cup apex _____
CUP POSITION REFERENCE DIMENSIONS Medial cup hole to CC bar reader (patient) _____
Lateral cup hole to CC bar reader (adaptor) _____
Medial cup hole to LAT bar reader (patient) _____
Lateral cup hole to LAT bar reader (adaptor) _____

The distance from the sternal notch to table top measurement is performed using the AP (anterior-posterior) bar and tightening and loosening knob 92 and reading the measurement at the AP bar reader 93. Preferably, the gradation and measurements are in millimeters, or other suitable dimensions. Since the measurements are relative, the actual height of ring 81 is not relevant, although it may be recorded. In accurately positioning the patient, it is desirable to make use of a laser marking system which is standard in radiation therapy. Three lasers form the system and are made to converge on a desired point on the patient, designating a "laser landmark." The laser landmark to the table top is measured using the AP bar. In addition, the sternal notch of the patient to the laser landmark is measured using the CC bar (cranial-caudal) by tightening and loosening knob 91 and reading the measurement at the CC bar reader 95.

Using the CC bar, the CC distance from the patient's sternal notch to the CC bar reader 95 is measured. In addition, the CC distance along the CC bar from the apex of the breast cup (hole 46) to the CC bar reader is measured. Then the CC distance between the sternal notch and the apex of the breast cup is calculated by calculating the difference between the measurements of the CC bar reader to the sternal notch and the CC bar reader to the breast cup apex.

Using the AP bar, the AP distance from the apex of the breast cup to the AP bar reader 93 is measured. Also using the AP bar, the AP distance from the sternal notch to the AP bar reader is measured. Finally, the AP distance from the sternal notch to the breast cup apex is calculated by calculating the difference of the above two measurements.

Using the LAT bar, the breast cup apex to the LAT bar reader 97 and the sternal notch to the LAT bar reader LAT distances are measured. Then the LAT distance between the breast cup apex and the sternal notch is calculated.

Additionally, the distance from the medial cup hole 44 to the CC bar reader is measured; the distance from the lateral cup hole 48 to the CC bar reader is measured; the distance from the medial cup hole 44 to the LAT bar reader is measured; and the distance from the lateral cup hole 48 to the LAT bar reader is measured.

In Table I, the cup number would preferably correspond to a specific cup in the cup library and thus could be used to create a phantom breast adaptor, which would be constructed in such a way to meet the contours of the standard phantom torso and have holes drilled in it to support TLDs in the same manner as the standard torso and with the same point of reference. It is noted that the construction of the phantom breast adaptor must not only match the selected cup's shape and size, but also must rest on a standard phantom upper torso so that the height of the adaptor corresponds to the height of the breast and the medial and lateral landmarks correspond to the breast. To achieve this, a phantom torso size corresponding to or just smaller than the patient's measurements is selected. Currently there are three standard phantom torso sites in the art, small, medium, and large. It is contemplated that the treatment center will use the same size phantom upper torso throughout the treatment of the patient. The phantom is made out of tissue equivalent materials that closely correspond to the radiation absorbent qualities of the different tissues found in the patient's torso (lungs, bones, soft tissue, etc). Construction of tissue equivalent phantoms is well known in the art and is not describe here. The phantom is positioned so that its sternal notch and laser landmark location match the patient's measured locations. As can be seen from FIG. 4, for example, the phantom has four adjustable legs 33 to provide the same height with respect to the table as the patient. The selected cup is then positioned on the phantom at the same breast cup apex, medial, and lateral positioning as on the patient. Clay may then by placed in the cup as needed so that the cup has a smooth mating surface with the phantom torso. The clay is then used to form a mold from which the phantom breast adaptor may be created.

Figure 3:
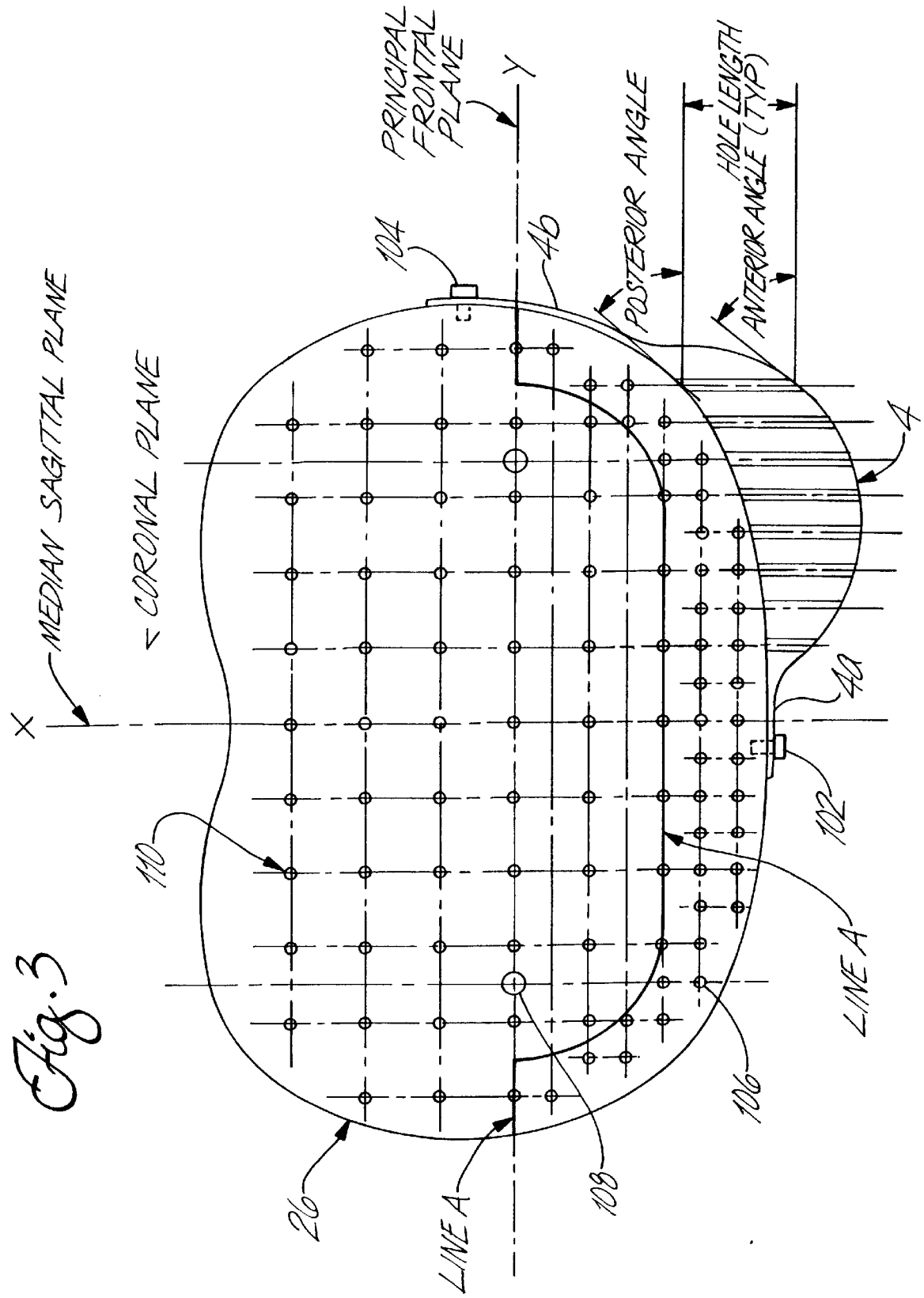
FIG. 3 is an explanatory diagram to show attachment of a phantom torso and phantom breast adaptor and alignment of TLD holding holes formed in the phantom and adaptor, in accordance with the invention.

The breast adaptor once created is then attached to the phantom using two nylon screws 102, 104, at medial 4a and lateral 4b portions of the adaptor 4, as shown in FIG. 3. The screws may pass through and hold the phantom breast adaptor 4 to the phantom upper torso 26. The adaptor is drilled in the anterior-posterior direction with a hole pattern that preferably matches the pattern of the holes in the phantom torso. The phantom torso has principal frontal holes 106 which are preferably of 5 mm diameter and located in a 1.5 cm center to center grid. Two holes 108 in the phantom torso are for the rods which hold the phantom slices together, and posterior holes 110 are preferably 5 mm holes on a 3 cm grid. Nuts 35 are placed on the ends of each rod that passes through the holes 108 and are tightened to hold the phantom slices together. The hole pattern for the phantom breast adaptor is preferably the same as the holes 106, e.g., 5 mm holes in a 1.5 cm grid. Preferably, the grid of the phantom breast adaptor is drilled to align with the phantom More specifically, the breast phantoms are drilled in the AP direction, even though radiation therapy phantoms are drilled in the CC direction. This facilitates the integration of the breast coordinate system with that of the phantom. This system is based on three mutually perpendicular planes. The two holes 108 are of 1 cm diameter and are the alignment holes between phantom slices. The line connecting these holes defines the principal frontal plane, (Y axis). A line vertical to this plane, bisects the Y axis which defines the median sagittal plane, and is designated as the X axis. Holes to the right of the X axis are positive, holes to the left are negative. Holes anterior to the Y axis are positive, holes posterior to that axis are negative. Frontal planes are also coronal planes. These planes are the interfaces between phantom slices.

Each breast is drilled in the AP direction with lines of holes coinciding with phantom slice interfaces. The convention adopted and well known in the art is that the slice number of the phantom defines the superior surface. Each row of holes has 1.5 cm spacing between holes and an integral number of 1.5 cm spaces between the medial sagittal plane and the first hole.

The system is designed for Harshaw-Bicron TLD chips $\frac{1}{8} \times \frac{1}{8} \times 0.035$ inches thick. A recess is molded at one end of chip holder tissue equivalent pins to make a close fit with the chip. The pins make close fits with the breast holes. Spacer pins are provided without recesses. These are colored pink for visual contrast with the brown chip holder pins. These make a sliding fit with the breast holes to facilitate pin removal from the breast.

A chart of the coordinates of the holes and hole length or other appropriate dimensions such as distance from median to sagittal plane, and anterior and posterior angles, for each row of holes in each breast is preferably provided by the manufacturer to the treatment facility so the radiologist may locate the chip precisely as desired within the phantom coordinate system. The number of rows of holes will vary with the breast size and shape. The number of holes in each row will also vary with breast size and shape. The phantom size and hole level may also be recorded.

Tissue equivalent pins are supplied to fill the holes of the breast adaptor with square ends, or with one end cut at 15°, 30° or 45°, or other angles, to match breast contours. Dimensions are taken at the center of each end of each hole. The square and angled ends of the tissue equivalent pins have recesses for TLDs. Most holes are drilled in the AP direction, but TLDs may be inserted into shallow holes at the sides. Holes not used for TLD chip holders are filled with blank tissue equivalent pins, including the shallow side holes.

The TLDs measure the actual radiation delivered to the TLD. By recording the radiation dosage delivered to each TLD and coordinating the TLD to the chart providing the coordinates of each hole, the treating professional can analyze the radiation delivered to different areas of the phantom and the breast adaptor and can compare that information with an ideal radiation dosage delivery treatment plan for the patient to be treated.

Thus, a method and apparatus for accurately treating and monitoring radiation dosages to a tumorous breast is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A brassiere for radiation treatment of a breast of a patient, the brassiere comprising a visually transparent cup having a predetermined shape adapted to hold the patient's breast in the predetermined shape and in a desired positions and means for fixing the cup to the patient's body with the cup over the patient's breast, whereby the patient's breast is consistently and repeatably held in the predetermined shape and desired position.

2. The brassiere of claim 1 wherein said cup comprises a semirigid material.

3. The brassiere of claim 1 further comprising means for shaping a contralateral breast, the shaping means adapted to hold the contralateral breast remote from the breast being treated with radiation.

4. The brassiere of claim 3 wherein said shaping means comprises a material having a property of being relatively rigid in shape at room temperature after a predetermined period of time and being relatively pliable for conforming to a desired shape under heating in a water bath.

5. The brassiere of claim 3 wherein said shaping means comprises a thermoplastic material.

6. The brassiere of claim 3 further comprising means attached to the shaping means for blocking radiation from the contralateral breast.

7. The brassiere of claim 6 wherein the means for blocking comprises a lead foil over the shaping means and wrapped partially around the shaping means.

8. The brassiere of claim 3 wherein the shaping means includes holes adapted to receive dosimeters for measuring radiation dosage to the skin of the contralateral breast and for monitoring effects of treatment on the contralateral breast.

9. The brassiere of claim 1 wherein the cup has a plurality of holes formed therein adapted to allow marking of the patient's skin to ensure consistent, repeatable placement of the cup, and to allow assessment of skin reaction to the radiation after each treatment.

10. The brassiere of claim 1 wherein the means for fixing the cup comprises means for positioning the cup at a predetermined location on the patient's upper thorax, the predetermined location being adapted from a radiation phantom for mapping dose distribution throughout the breast being treated and tissue surrounding the breast being treated.

11. The brassiere of claim 1 further comprising means for marking the patient's skin when the cup is positioned in the predetermined shape and desired position, the marking means is adapted to allow the cup to be placed consistently and repeatable in the same position on the patient's upper thorax.

12. The brassiere of claim 1 wherein the transparent cup is selected from a set of brassiere cups for use in a radiation treatment of the patient's breast, the set comprising a plurality of brassiere cups comprising at least two different breast sizes and at least two different predetermined shapes in each breast size.

13. The set of brassiere cups according to claim 12 wherein there are cups for each of A, B, C, D, DD and DDD, for both left and right breasts and six different shapes for each size cup for each side totaling 72 different cups.

14. The set of brassiere cups according to claim 13 wherein the set contains custom made cups different from the 72 cups.

15. A set of breast adaptors for a radiation phantom for measuring radiation dosage effects, the breast adaptors comprising bodies of material having shapes and sizes corresponding to different shapes and sizes of breasts and having means formed therein for receiving tissue equivalent pins to measure radiation dosages, and having means adapted to releasably mounting the bodies to a radiation therapy phantom corresponding to a torso.

16. The set of breast adaptors of claim 15 wherein the tissue equivalent pins comprise means for receiving thermoluminescent dosimeters.

17. The set of breast adaptors of claim 15 wherein the means formed therein for receiving defines holes disposed in a pattern corresponding to a pattern of holes in the radiation phantom.

18. A method of radiation therapy for a tumorous breast, the method comprising the steps of:
(a) placing a visually transparent cup over a patient's tumorous breast and aligning the tumorous breast with respect to a fixed reference using the visually transparent cup and a measuring device to determine the breast's location in three dimensional space with respect to the fixed reference;
(b) removing the patient from the fixed reference and placing a phantom including a phantom breast adapted to monitor radiation dosage on the fixed reference and aligning it with respect to the fixed reference in the same location as the patient's breast was;
(c) applying radiation to the phantom breast in accordance with a selected radiation treatment plan for the tumorous breast;
(d) analyzing radiation dosage produced by the radiation treatment to the phantom breast and, if necessary, revising the treatment plan and repeating steps (b) and (c) above until the radiation results are as desired;
(e) removing the phantom and replacing the patient with the cup over the patient's tumorous breast at the same location with respect to the fixed reference; and
(f) treating the patient's tumorous breast with the selected radiation treatment plan.

19. The method of claim 18 further comprising a step of repeating steps (a) to (f) for a duration of a therapy program.

* * * * *

UNITED STATES PATENT AND TRADEMARK OFFICE
CERTIFICATE OF CORRECTION

PATENT NO. : 5,769,779
DATED : June 23, 1998
INVENTOR(S) : Samuel W. Alderson

It is certified that error appears in the above-identified patent and that said Letters Patent is hereby corrected as shown below:

Column 6, line 14, replace "has Velcros" with -- has a Velcro® --.
Column 6, line 17, replace "evidence" with -- evident --.
Column 9, line 25, replace "describe" with -- described -- .
Column 9, line 32, after "may then" replace "by" with -- be --.
Column 9, line 54, after "phantom" insert -- torso's grid. --.
Column 10, line 59, replace "positions" with -- position --.
Column 10, line 62, replace "repeatably" with -- repeatedly --.
Column 11, line 36, replace "repeatably" with -- repeatedly --.

Signed and Sealed this

Twenty-fourth Day of August, 1999

Attest:

Q. TODD DICKINSON

*Attesting Officer*  *Acting Commissioner of Patents and Trademarks*